United States Patent [19]

Sawai et al.

[11] Patent Number: 5,336,688
[45] Date of Patent: Aug. 9, 1994

[54] COMPOSITION CONTAINING ORGANOGERMANIUM COMPOUND AND IMMUNITY ADJUSTING AGENTS COMPRISING THE COMPOSITIONS

[75] Inventors: Kiichi Sawai, Funabashi; Masayasu Kurono; Juichi Awaya, both of Nagoya; Akio Kojima, Kasugai; Hideako Ninomiya; Yoshiro Ishiwata, both of Nagoya; Masahiro Nakajima, Gifu, all of Japan

[73] Assignee: Sanwa Kagaku Kenkyusho Co., Ltd., Nagoya, Japan

[21] Appl. No.: 8,876

[22] Filed: Jan. 25, 1993

Related U.S. Application Data

[60] Division of Ser. No. 428,675, Oct. 30, 1989, abandoned, which is a continuation-in-part of Ser. No. 224,279, Jul. 25, 1988, Pat. No. 4,889,715, which is a continuation-in-part of Ser. No. 809,819, Dec. 17, 1985, abandoned.

[30] Foreign Application Priority Data

Dec. 25, 1984 [JP] Japan .................. 59-272057

[51] Int. Cl.$^5$ .................. A01N 55/02; A61K 31/28
[52] U.S. Cl. .................. 514/492; 514/184; 424/78.08
[58] Field of Search .................. 514/492, 184; 424/78.08

[56] References Cited

U.S. PATENT DOCUMENTS 4,322,402  3/1982  Ishikawa et al. .................. 514/492
4,889,715  12/1989  Sawai et al. .................. 524/21

FOREIGN PATENT DOCUMENTS 147932  11/1979  Japan .................. 514/492
118015  9/1981  Japan .................. 514/492

OTHER PUBLICATIONS

The Merck Index, 9th Ed., Merck & Co., Inc., Rahway, N. J. 1976, pp. 564, 701 & 702.

Primary Examiner—Nathan M. Nutter
Attorney, Agent, or Firm—Nikaido, Marmelstein, Murray & Oram

[57] ABSTRACT

A composition comprising an organogermanium compound represented by the formula

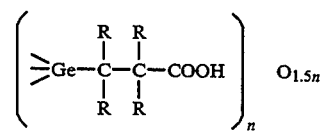

wherein n is an integer of 1 or more, R is hydrogen, alkyl, —COOH, —COOR′, phenyl,

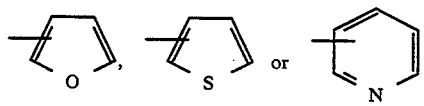

and R′ is a lower alkyl and a high molecular carrier, as well as an immunity adjusting agent comprising the composition.

2 Claims, 14 Drawing Sheets

COMPOSITION CONTAINING ORGANOGERMANIUM COMPOUND AND IMMUNITY ADJUSTING AGENTS COMPRISING THE COMPOSITIONS

This application is a continuation division of application Ser. No. 07/428,675, filed Oct. 30, 1989, now abandoned, which is a continuation-in-part of application Ser. No. 224,279, filed Jul. 25, 1988, now U.S. Pat. No. 4,889,715, which was a continuation-in-part of application Ser. No. 809,819, filed Dec. 17, 1985, abandoned.

BACKGROUND OF THE INVENTION

1. Field of the Invention

The present invention relates to a composition containing an organogermanium compound and an immunity adjusting agent comprising the composition. The organogermanium compound is represented by the formula

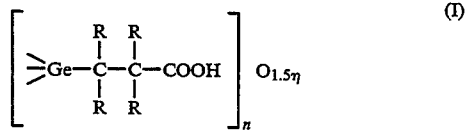

wherein n is an integer of 1 or more, R is hydrogen, alkyl, —COOH, —COOR', phenyl,

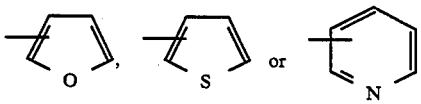

and R' is a lower alkyl.

2. Related Arts

The organogermanium compound (polymer) represented by Formula I has been watched with great interest in recent years, due to attractive pharmacological activities thereof and thus various derivatives have been synthesized.

However, these organogermanium compounds as proposed have a common disadvantage of that it is not so stable to water. Namely, when such an organogermanium compound is prepared through a hydrolysis of trichlorogermylpropionic acid, some different organogermanium compounds will be formed, as disclosed in Examined Jap. Pat. Appln. Gazette Nos. 2498/1971 and 53800/1982 as well as Unexamined Jap. Pat. Appln. Gazette No. 102895/1982. It means a fact that a product will be made different, due to a slight difference in term or condition for the hydrolysis reaction. Therefore, such a possibility is to be estimated that a certain product may change into another product, when the former will be suspended or dissolved in water and a generation of this phenomenon has actually been reported (Examined Jap. Pat. Appln. Gazette Nos. 53800/1982 and 18399/1984).

The inventors have carefully studied on pharmacological activities of the various organogermanium compounds represented by said Formula I, which have been prepared by a common process but under a different synthetic condition, to find that each compound shows a remarkable difference in degree of the pharmacological activity. Now, it is, of course, required to obtain specific organogermanium compounds which show a high and stable pharmacological activity, for utilizing same as an effective component for a pharmaceutical agent. However, it has further been confirmed by the inventors on the compounds of Formula I and more particularly those, wherein all of the substituents R in the Formula is hydrogen, that a polymerization degree varies due to a slight difference in synthetic conditions therefor, that a form as the pharmaceutical agent is limited to a solid one only, since an intermolecular bond therein is easily severed or broken due to a slight change in environment or atmosphere, and that a stable appearance of pharmacological activities inherent to the compound can not be expected, since at least partial decomposition thereof occurs prior to reach to a desired absorption area in a living body.

Hitherto, a large number of reports to the effect that the organogermanium compounds in question have an immunity accerating action as one of those pharmacological actions has been issued, but each of such compounds has not only been employed for developing a pharmaceutical agent, due to its low stability and other difficulties but also been considered as a harmful substance to various diseases or disorders concerning to an immunity acceration system.

However, the inventors have now found through their various studies that the organogermanium compounds in question show great effectivity on various immunity disorders, namely both of the immunity inhibition system disorders and the immunity acceration system disorders and thus the "immunity accerating action" which has hitherto been reported and widely been accepted is not right and should be corrected to an —immunity adjusting or regurating action.

OBJECT AND SUMMARY OF THE INVENTION

Therefore, an object of the invention is to provide a composition, in which at least one of the compounds of Formula I is phisico-chemically and pharmacologically stabilized.

Another object of the invention is to provide an immunity adjusting agent useful as a therapeutic agent for various immunity disorders due to an abnormal increase or decrease of immunity function in living bodies.

According to the invention, the objects can be attained by a composition comprising an organogermanium compound represented by the formula

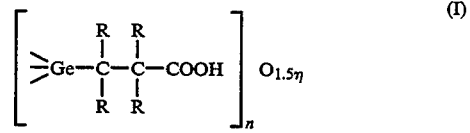

wherein R has the meaning as referred to and a high molecular carrier for pharmaceutical agents, as well as an immunity adjusting agent comprising the composition.

The organogermanium compound composed in the composition or the immunity adjusting agent according to the invention can be obtained by treating in a halogenohydroacid, germanium dioxide with hydrophosphorous acid or a salt thereof, reacting the resulting halogenogermanium-phosphoric acid complex with a compound represented by the formula

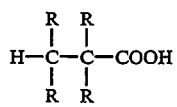

wherein R has the meaning as referred to dissolving the resulting compound represented by the formula

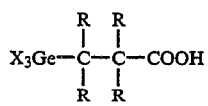

wherein R has the meaning as referred to and X is a halogen into acetone or another organic solvent having a solubility to water, and adding water into the solution.

The high molecular carrier composed in the composition or the immunity adjusting agent according to the invention serves also to stabilize the organogermanium compound as the main component and a natural high molecular substance, synthetic high molecular substance, proteinic substance or saccharoid may be employed therefor. It is preferable to compose the carrier in an amount ranging from 0.01 to 200 parts by weight, for instance 0.05 to 5 parts by weight based on 1 weight part of the organogermanium compound. As the natural high molecular substance, biological one, for instance gelatin, pepsin, serum albumin (cattle, horse or human origin), globulin, protamine and a mixture thereof may be listed. As the synthetic high molecular substance, polyethylene glycol and the like glycols; hydroxypropylcellulose, hydroxypropylmethylcellulose and the like cellulosic high molecular substances, polyvinylpyrrolidone and the like vinylic high molecular substances; and polyacryloamide and the like acrylic high molecular substances may be listed. As the proteinic high molecular substance, in general, additives for culture mediums, for instance peptone, polypeptone, yeast extract, tryptone, tryptose, dextrose and the like may be listed. As the saccharoid, lactose, refined sugar, glucose, starch, cellulose and the like may be listed.

The compounds as shown in following Table 1 may be listed as exemplary organogermanium compounds to be employed for the invention.

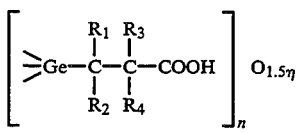

TABLE 1

| Compound number | $R_1$ | $R_2$ | $R_3$ | $R_4$ | Crystal form and dec. temperature |
|---|---|---|---|---|---|
| 1 | H | H | H | H | white needle, 240° C. |
| 2 | $CH_3$ | H | H | H | white crystal, more than 300° C. |
| 3 | $C_2H_5$ | H | H | H | white crystal, more than 300° C. |
| 4 | $(CH_2)_2CH_3$ | H | H | H | white crystal, more than 300° C. |
| 5 | $(CH_2)_4CH_3$ | H | H | H | white crystal, more than 300° C. |
| 6 | $(CH_2)_{12}CH_3$ | H | H | H | white crystal, 172–176° C. |
| 7 | H | H | $CH_3$ | H | white needle, more than 300° C. |

TABLE 1-continued

| Compound number | $R_1$ | $R_2$ | $R_3$ | $R_4$ | Crystal form and dec. temperature |
|---|---|---|---|---|---|
| 8 | H | H | $C_2H_5$ | H | white crystal, more than 300° C. |
| 9 | $CH_3$ | H | $CH_3$ | H | white crystal, more than 300° C. |
| 10 | $CH_3$ | $CH_3$ | H | H | white crystal, more than 300° C. |
| 11 | COOH | H | H | H | white crystal, more than 300° C. |
| 12 | $C_6H_5$ | H | H | H | white crystal, more than 300° C. |

For making the composition into a pharmaceutical agent, a filling, binder, disintegrator and the like aids may be composed, but such aid should be one showing no reactivity to the organogermanium compound as the main component and no activity to a delayed type immunity response reaction test, from a pharmacological view point.

A dosing form as the pharmaceutical agent may freely be selected to make the composition into a solid one, for instance a tablet, capsule, granule, infinitesimal grain, powder, suppository, dry syrup or the like; a solution one, for instance an injection, orally dosing solution agent, external lotion or the like; or a semi-solid one, for instance an externally applying cream, jelly or the like.

It is preferable to dose for human in an amount of 0.3 to 20 mg/kg, for instance 1 mg/kg, as an amount of the organogermanium compound.

EFFECT OR ADVANTAGE OF THE INVENTION

According to the invention, the organogermanium compound as the main component is effectively stabilized to allow free selection in dosing form thereof as the pharmaceutical agent, so that pharmacological activities of the organogermanium compound can sufficiently be utilized.

The immunity adjusting agent of the invention shows a powerful and stable physiological activity through an immunity system and is useful as a treatment for various self immunity disorders and is of particular significance in the treatment of acquired immune deficiency syndrome (AIDS) and hepatitis.

BRIEF DESCRIPTION OF THE DRAWINGS

The following

FIG. 1 is an IR spectrum of the original or non-treated oregano-germanium compound of this invention;

FIG. 2 is an IR spectrum of a composition of this same compound and a serum albumin which has been stored for 30 days prior to the spectrum being taken;

FIG. 3 is an IR spectrum of a composition of this same compound and a hydroxypropyl cellulose which has been stored for 30 days prior to the spectrum being taken;

FIG. 4 is an IR spectrum of a composition of this same compound and a gamma-globulin which has been stored for 30 days prior to the spectrum being taken;

FIG. 5 is an IR spectrum of a composition of this same compound and pepsin which has been stored for 30 days prior to the spectrum being taken;

FIG. 6 is an IR spectrum of a 4% aqueous solution of this same original compound which ha been stored for 24 hours;

FIG. 7 is an IR spectrum of a 4% aqueous solution of this same original compound which has been stored for 60 hours;

DETAILED DESCRIPTION OF PREFERRED EMBODIMENTS

The invention will now be explained with reference to stability test examples, pharmacological test examples and pharmaceutical agent preparation examples.

Stability Tests

1) Physics-chemical stability test a) To 5 ml of 4% cattle serum albumin solution, 200 mg of the organogermanium compound (Compound No. 1 in Table 1) were added and dispersed therein by a mixer to prepare a composition of the invention (4% suspension of the organogermanium compound).

The suspension was stored in a thermostat kept at 25° C., sampled out after a lapsed time of 1, 3, 9, 15 and 30 days and filtered. Each resulting solid substance was washed with acetone and ethanol and then dried for 1 hour at 105° C.

As to the resulting dried substance, the stability thereof was checked by measuring its IR spectrum, using the potassium bromide tablet method.

Figure 1:
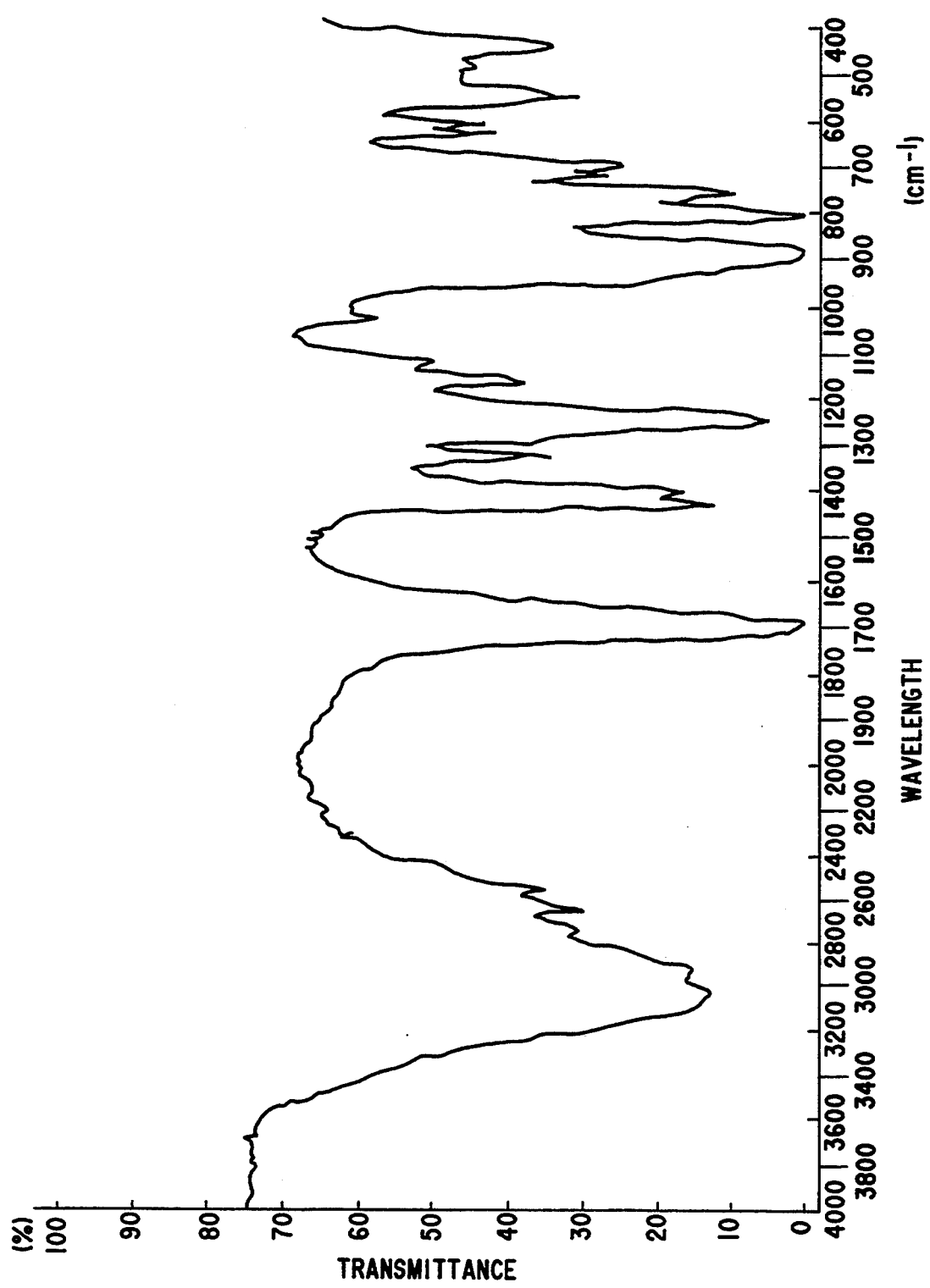
FIGS. 1–7 are all infra red spectra of various compositions, as noted, containing the compound listed as compound 1 in table 1 above.

An IR spectrum of the original or non-treated organogermanium compound is shown in FIG. 1 and has a characteristic absorption spectrum at 1695, 1435, 1255, 890 and 805 cm, and thus the stability of each sample in question was judged on the basis of the characteristic absorption spectrum.

Figure 2:
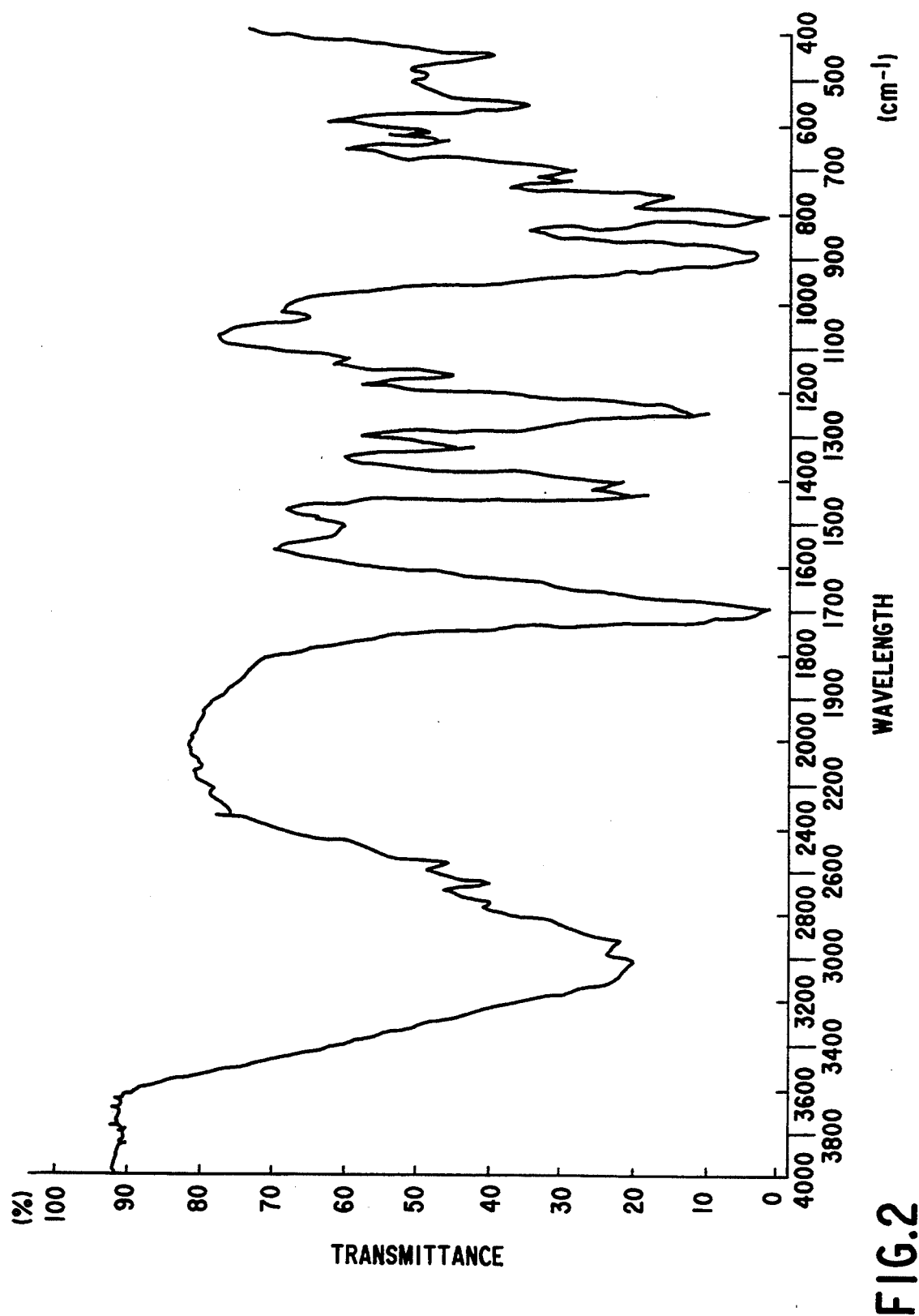

The tested composition was kept in stable state, even after a time lapse of 30 days (see FIG. 2).

Figure 3:
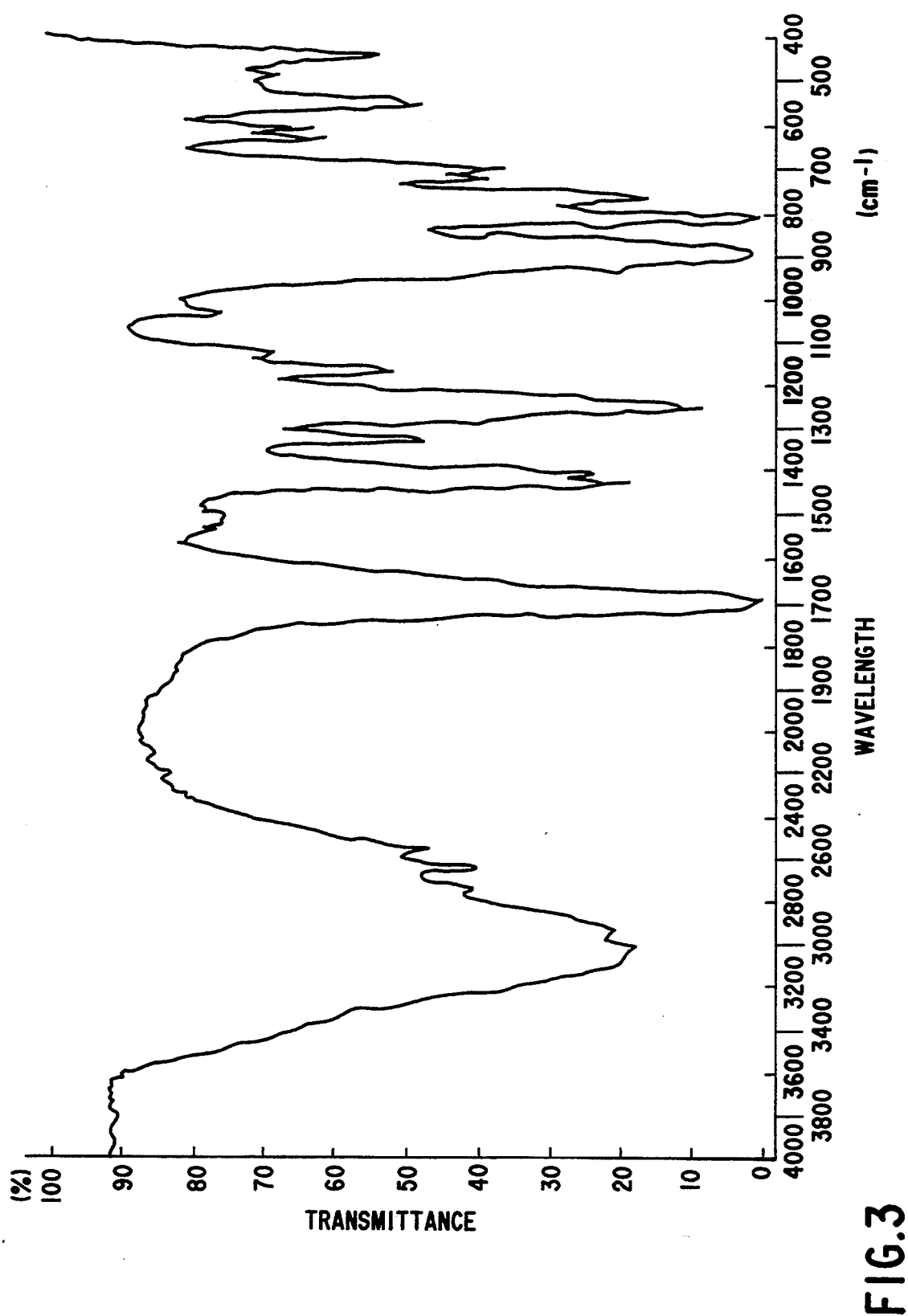
Figure 4:
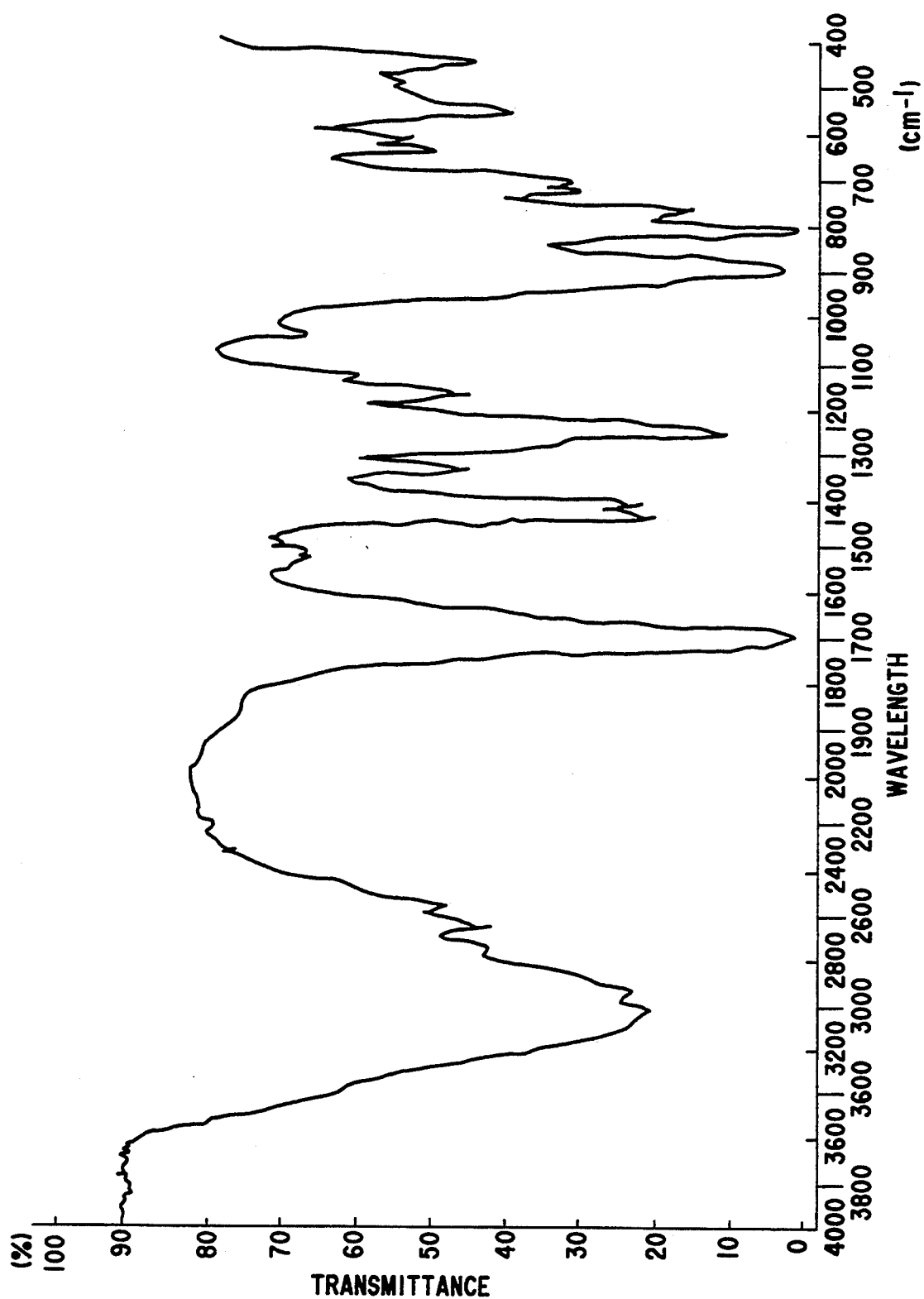
Figure 5:
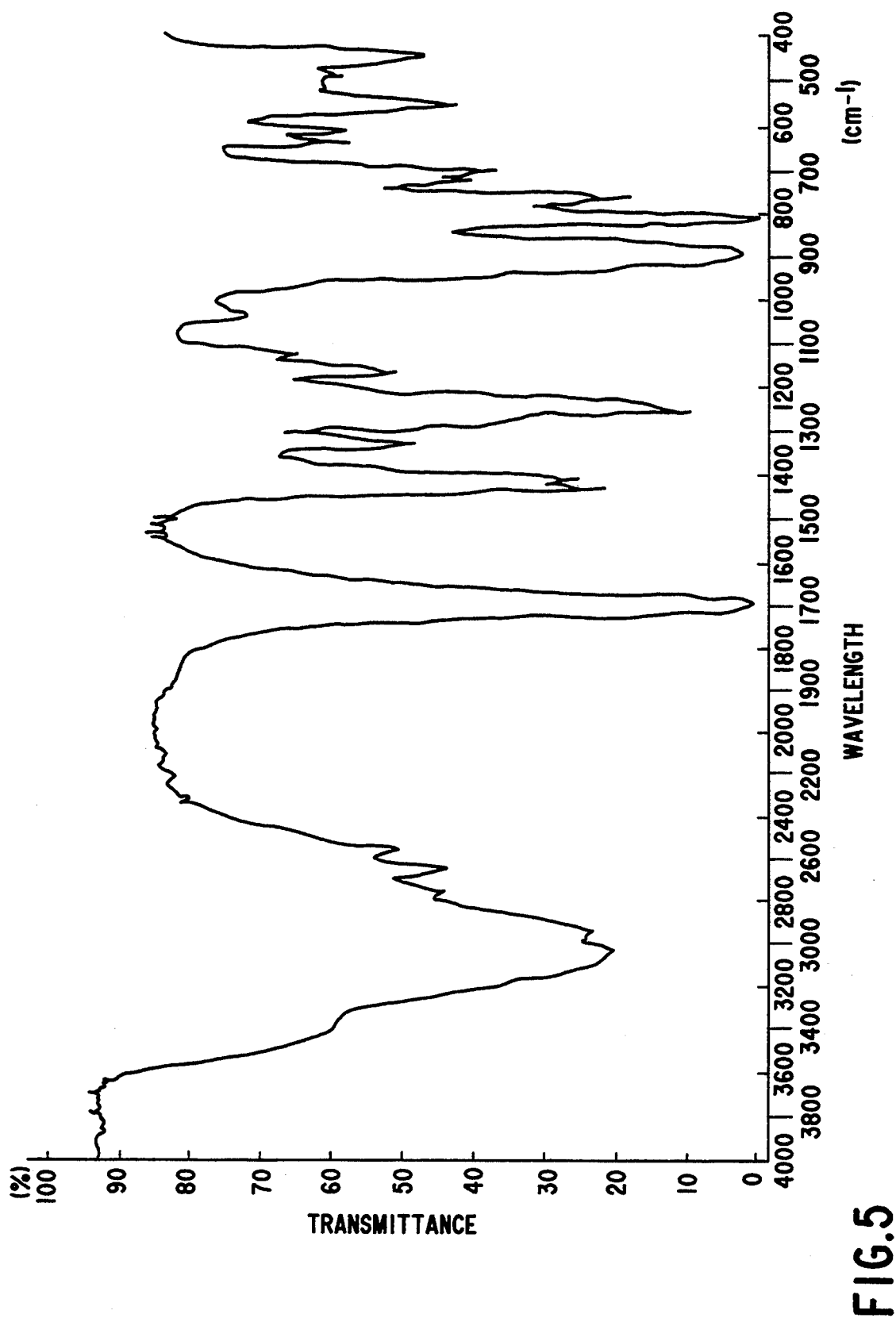
Figure 6:
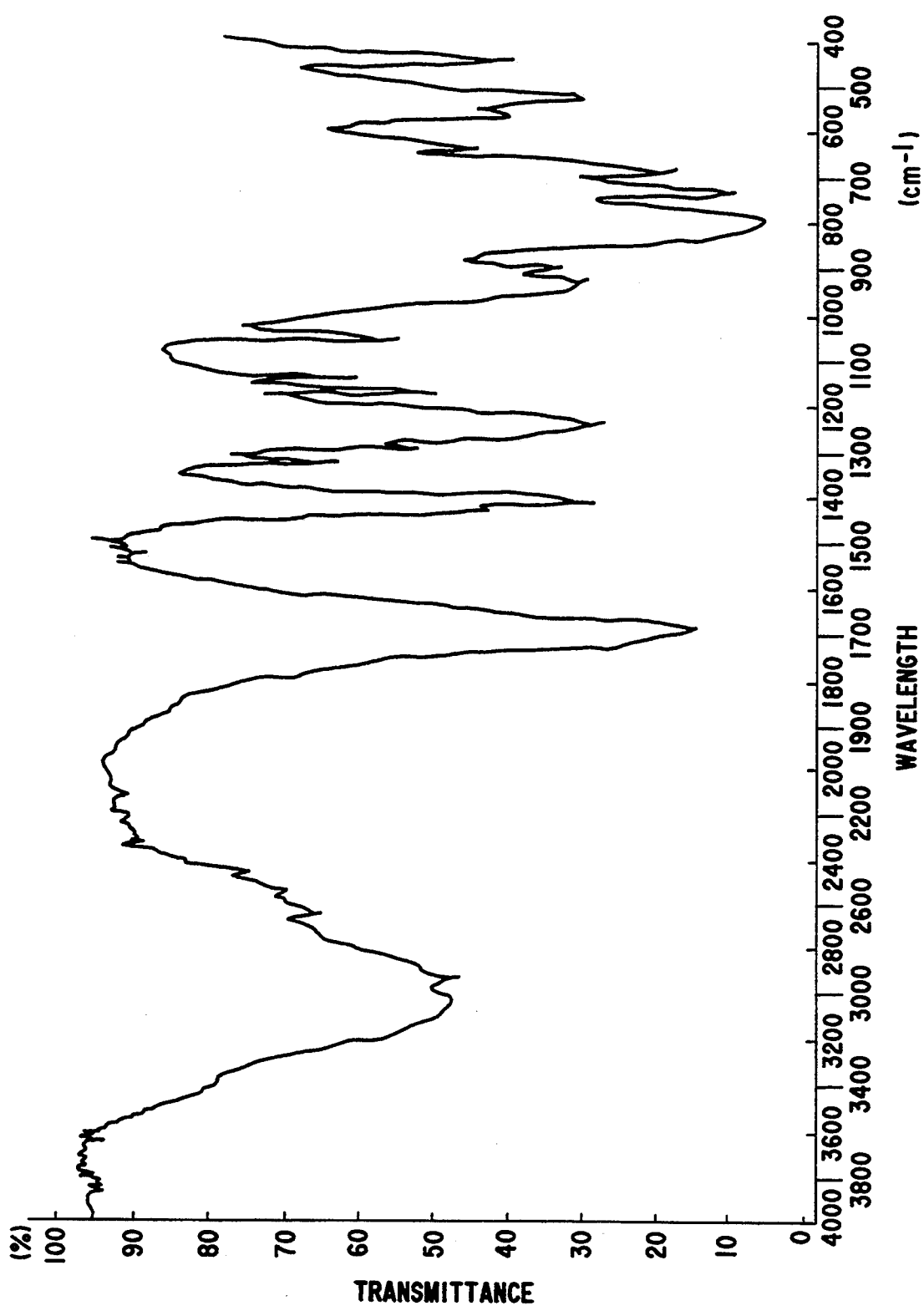
Figure 7:
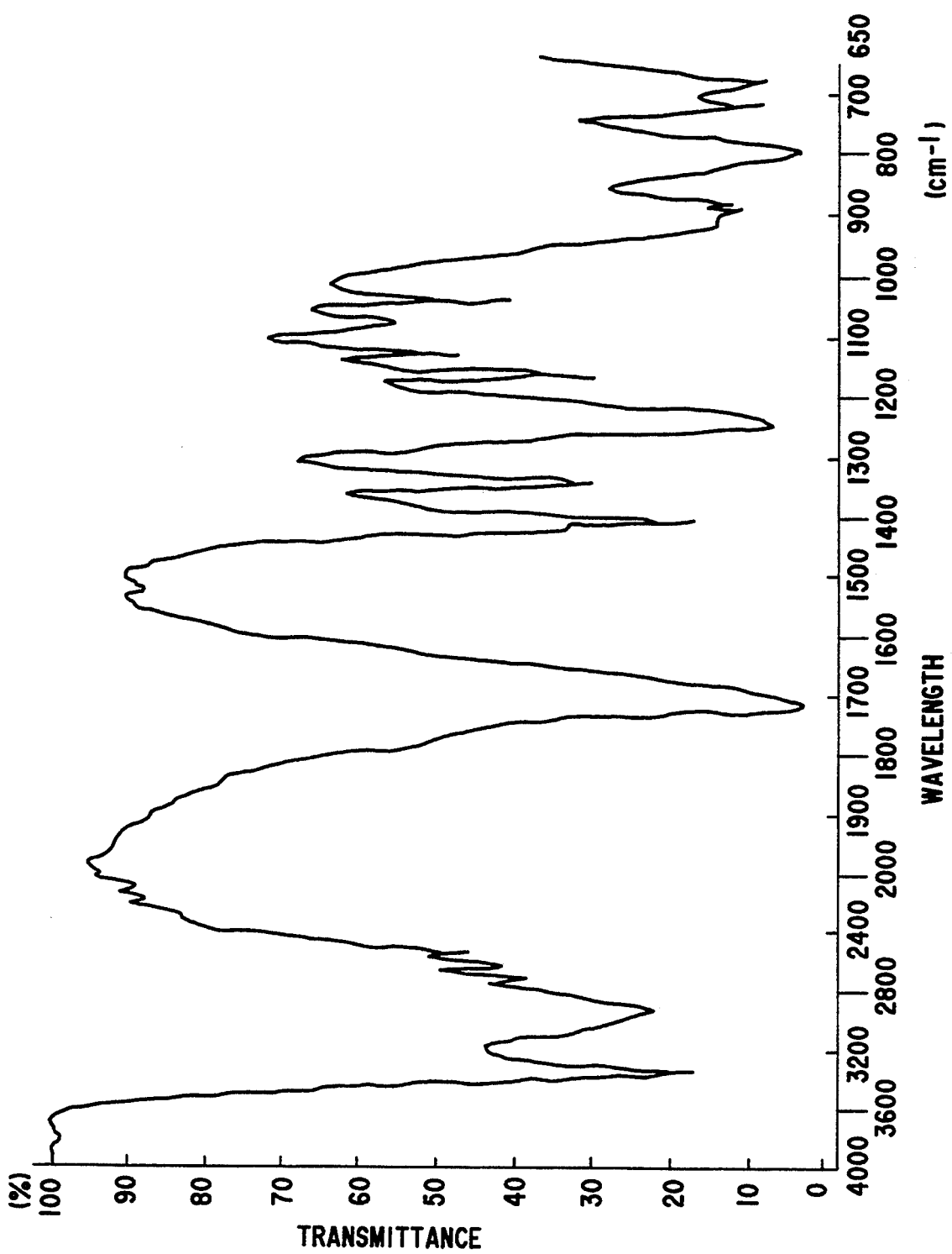

As control, a composition was prepared with use of water in lieu of the serum albumin and its stability was measured in a manner similar to the above to find that a disturbance in the absorption spectrum was first observed on the sample having a lapsed time of 24 hours (see FIG. 6) and that the disturbance was further increased on the sample after a lapsed time of 60 hours (see FIG. 7). This shows that a modification or decomposition occurs in the organogermanium compound in control composition.

b) Compositions according to the invention were prepared as in the case of said Item a but with use of hydroxypropylcellulose, gamma-globulin and pepsin, respectively, in lieu of the serum albumin. Each of the compositions was tested as in the case of said Item a to find that the organogermanium compound is kept in stable state, by virtue of coexsistence with such a high molecular weight carrier (see FIGS. 3 to 5).

A similar result was obtained on various compositions, wherein gelatin, protamine, hydroxypropylmethylcellulose, polyvinylpyrrolidone, polyacrylamide, peptone, polypeptone, yeast extract, trypton, tryptose, dextrose, lactose, refined sugar, glucose, starch or cellulose was employed as the high molecular carrier for the organogermanium compound, in lieu of the serum albumin.

2. Biological stability test

Effect to delayed type hyperergy (DTH) on cancered mouse After implantation of $10^6$ cells of sarcoma 180 cancer cell in an abdominal canal of ICR mice, $10^6$ corpuscles of sheep red blood corpuscle (SRBC) were intravenously injected for sensitization. After a lapsed time of 4 days from the implantation, $2 \times 10^8$ cells of SRBC were injectionally dosed at a heel of a hind leg of said mice to cause the DTH. After 24 hours from the dosage, a degree of swelling was checked by measuring a thickness of the heel.

On the other hand, various testing compositions (Nos. 1 to 10 in following Table 2) were prepared with use of various high molecular carrier and adding the organogermanium compound (Compound No. 1 in said Table 1), so as to make its concentration of 1 mg/10 ml, and a control testing composition was prepared by adding the organogermanium compound in water to make its concentration of 1 mg/10 ml. Each of the compositions was orally dosed to each mouse, respectively before 4 days before the cancer cell (Sarcoma 180) implantation and in an amount of 1 mg/10 ml/kg.

Results are shown in the following Table 2. From the table, it can be seen that each of the compositions according to the invention increases the DTH of the cancered mouse but the control composition is not effective in the dosing amount of 1 mg/kg.

TABLE 2

| | heel swelling ($\times$ 0.01 mm) mean value $\pm$ standard deviation value |
|---|---|
| Non-treated | 114.1 $\pm$ 11.5 |
| Cancered | 57.2 $\pm$ 7.6 |
| Control composition | 57.0 $\pm$ 6.3 |
| Composition of the invention | |
| No. 1 (5% cattle serum albumin) | 75.3 $\pm$ 6.3 |
| No. 2 (0.5% gelatin) | 99.9 $\pm$ 7.3 |
| No. 3 (1% pepsin) | 109.5 $\pm$ 9.2 |
| No. 4 (cattle fetal serum) | 100.8 $\pm$ 8.4 |
| No. 5 (10% horse serum albumin) | 96.15 $\pm$ 5.6 |
| No. 6 (0.5% polyethylene glycol) | 105.2 $\pm$ 8.2 |
| No. 7 (0.5% hydroxypropylcellulose) | 98.3 $\pm$ 5.8 |
| No. 8 (0.5% polyvinylpyrrolidone) | 108.3 $\pm$ 2.1 |
| No. 9 (0.5% polyacryloamide) | 113.1 $\pm$ 2.8 |
| No. 10 (1% peptone) | 92.6 $\pm$ 5.4 |

Pharmacological Test Example 1

Influence of organogermanium compound on antibody production ability in normal mouse a) object An effect of the organogermanium compound (Compound No. 1 in Table 1) is checked by sensitizing mice with an antibody in an amount of generating a sufficient antigen excitement to develop an immunity response in maximum level or not developing a sufficient immunity response due to no sufficient antigen excitement.

b) operation

To each group of ICR mice (age, 5 weeks), $2 \times 10^8$ and $2 \times 10^7$ corpuscles of sheep red blood corpuscle (SRBC) as an antibody were venously injected for sensitization in a tail vein of the mice. Then, immediately, the organogermanium compound dissolved in 4% cattle serum albumin solution was orally dosed to the sensitized mice in an amount of 0.1, 1.0 and 10 mg/kg, respectively. After 4 days from the sensitization, spleen cells were extracted to measure a number of PFC therein, which was made as an index of the antibody productivity.

Figure 8A:
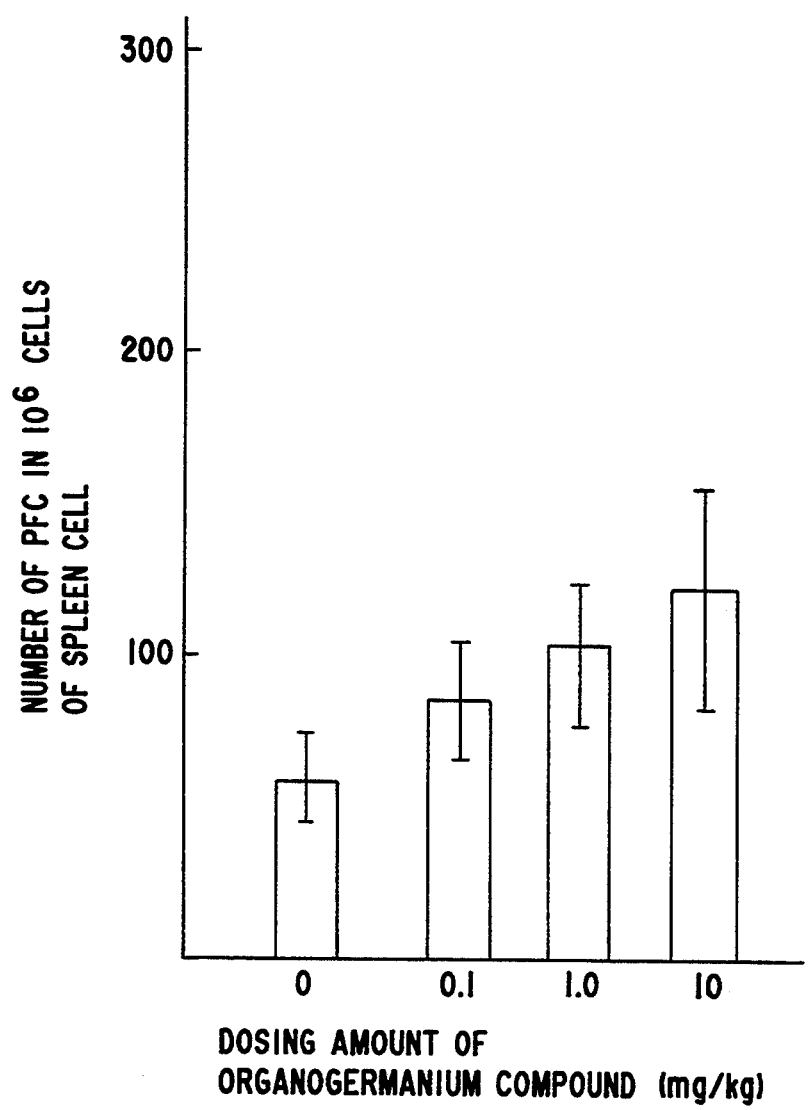
FIG. 8a is a series of graphs showing the influence of this same original compound on the ability to produce antibodies when normal mice are sensitized with SRBC of $2 \times 10^8$.
Figure 8B:
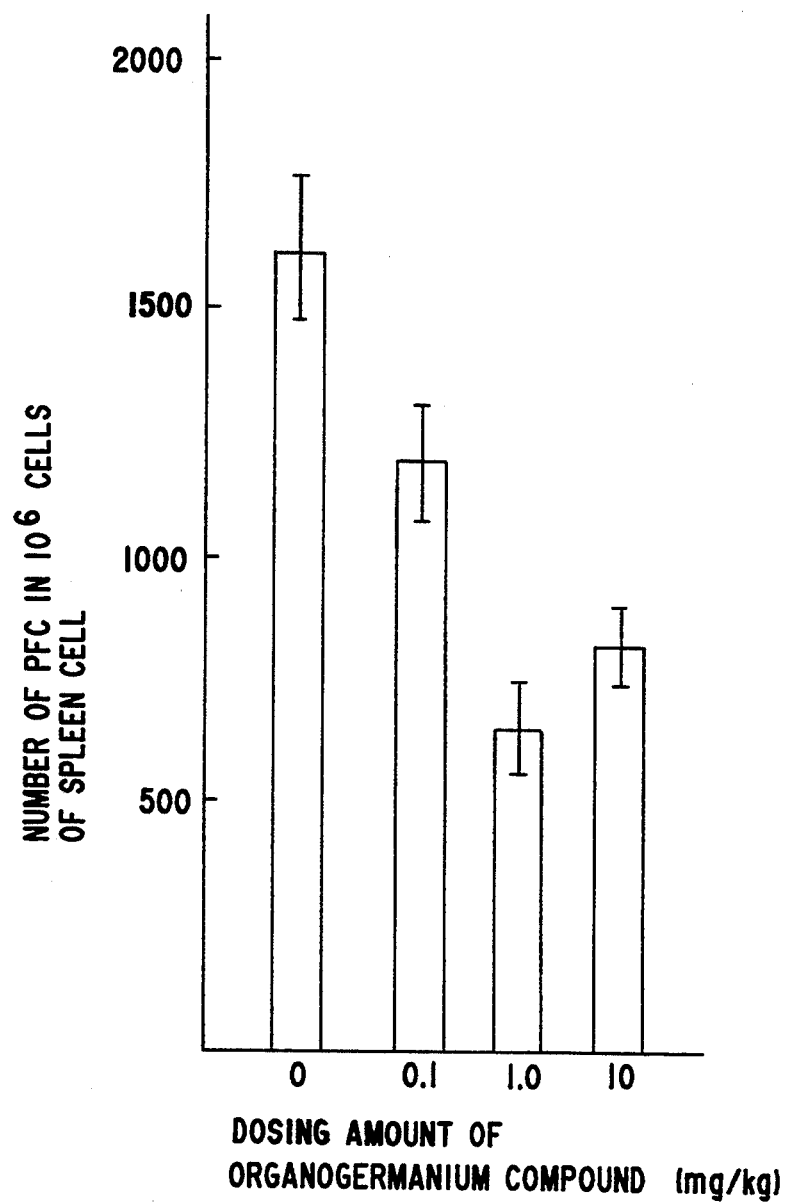
FIG. 8b is a series of graphs showing the influence of this same original compound on the ability to produce antibodies when normal mice are sensitized with SRBC of $2 \times 10^7$.

Results in the experimental group sensitized with $2 \times 10^8$ corpuscles of SRBC and the other group sensitized with $2 \times 10^7$ corpuscles of SRBC are shown in FIGS. 8a and 8b, respectively. From the figures, such a tendency can be seen that a spleen cell PFC is decreased, in the former group but is increased in the latter group.

These facts apparently show that the organogermanium compound reveals an immunity adjusting action.

Pharmacological Test Example 2

Influence of organogermanium compound on antibody production ability in cancered mouse a) Object Similar to the object as referred to in the Pharmacological Test Example 1.

b) operation $2 \times 10^6$ cells of a mouse tumor cell (Sarcoma 180) were implanted under a skin of a side part of ICR male mice to form a solid cancer. The organogermanium compound (Compound No. 1 in Table 1) dissolved in 4% cattle serum albumin solution was orally dosed to the cancered mice for 5 days after lapsed 9 days from the implantation, $2 \times 10^8$ corpuscles of SRBC were injected in a tail vein of the mice for sensitization. After 4 days from the sensitization, spleen cells were extracted to measure of PFC therein, which was made as an index of the antibody productivity.

c) Results and consideration

Figure 9:
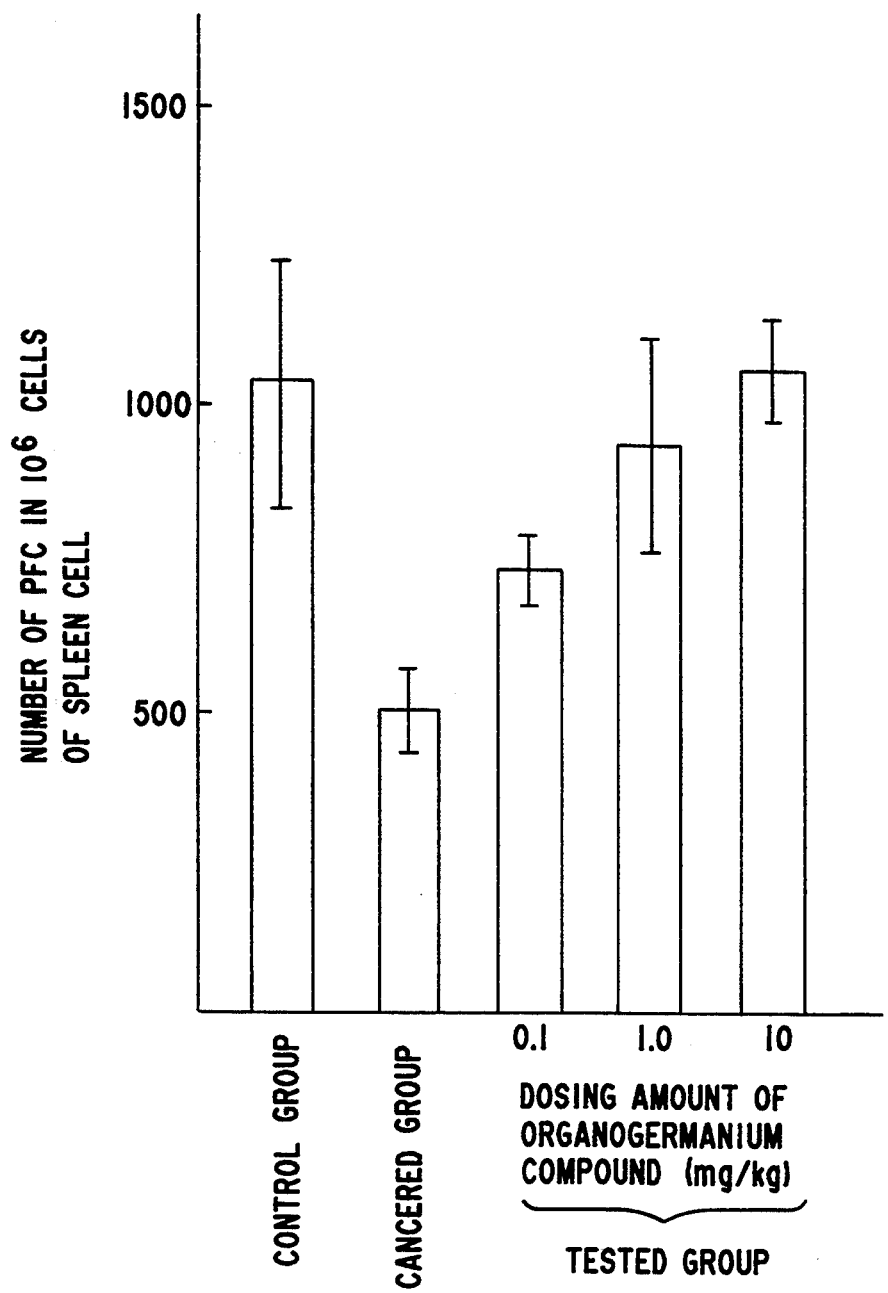
FIG. 9 is a series of graphs showing the influence of this same original compound on the ability of cancered mice to produce antibody.

Results are shown in FIG. 9. As seen from the figure, it has been found that the antibody production ability reduces due to generation of the cancer, but by dosing the organogermanium compound, the antibody production ability will become recovered towards a normal level, depending on a dosing amount of the compound.

By taking this result and the result as shown in FIG. 8a into consideration, it is apparent that the organogermanium compound develops an immunity adjusting action.

Pharmacological Text Example 3

Influence of the organogermanium compound on antibody production ability in culture system for mouse lymphocyte a) Object Influence of the organogermanium compound (Compound No. 1 in Table 1) on SRBC is checked on a culture system of lymphocytes extracted from NZB/W $F^1$ mice who generates a self immunity disease due to functional reduction of suppressor T cells as well as normal BALB/C mice.

b) operation

Spleen lymphocytes were extracted from NZB/W $F_1$ male mice (age, 14–15 weeks) and BALB/C male mice (age, 10–13 weeks), washed with a Hanks solution, dispersed through a 100 mesh filter and then washed twice with the Hanks solution. The resulting lymphocytes were dispersed in a 10% foetal calf serum to which was added BPMI 1640 culture medium (including 2-mercaptoethanol in $5 \times 10^5$ M) and containing the organonogermanium compound and the lymphocyte concentration of the dispersion was adjusted with a Turk solution into $1.2 \times 10^7$ corpuscles/ml.

For comparison, SRBC was washed twice with the Hanks solution and then dispersed in a manner similar to the above into the 10% foetal calf serum to which was added RPMI culture medium containing the organogermanium compound, and the concentration of the SRBR was adjusted into $1.2 \times 10^7$ corpuscles/ml.

Each 0.5 ml of said lymphocyte suspended medium and said SRBC suspended medium was sampled and mixed. The mixture was charged in a microplate and cultivated for 4 to 5 days at 37° C. under 5% $CO_2$. Thereafter, an anti-SRBC antibody produced cell number was measured with a slide method, as a plague forming cell number.

c) Results and consideration

Figure 10A:
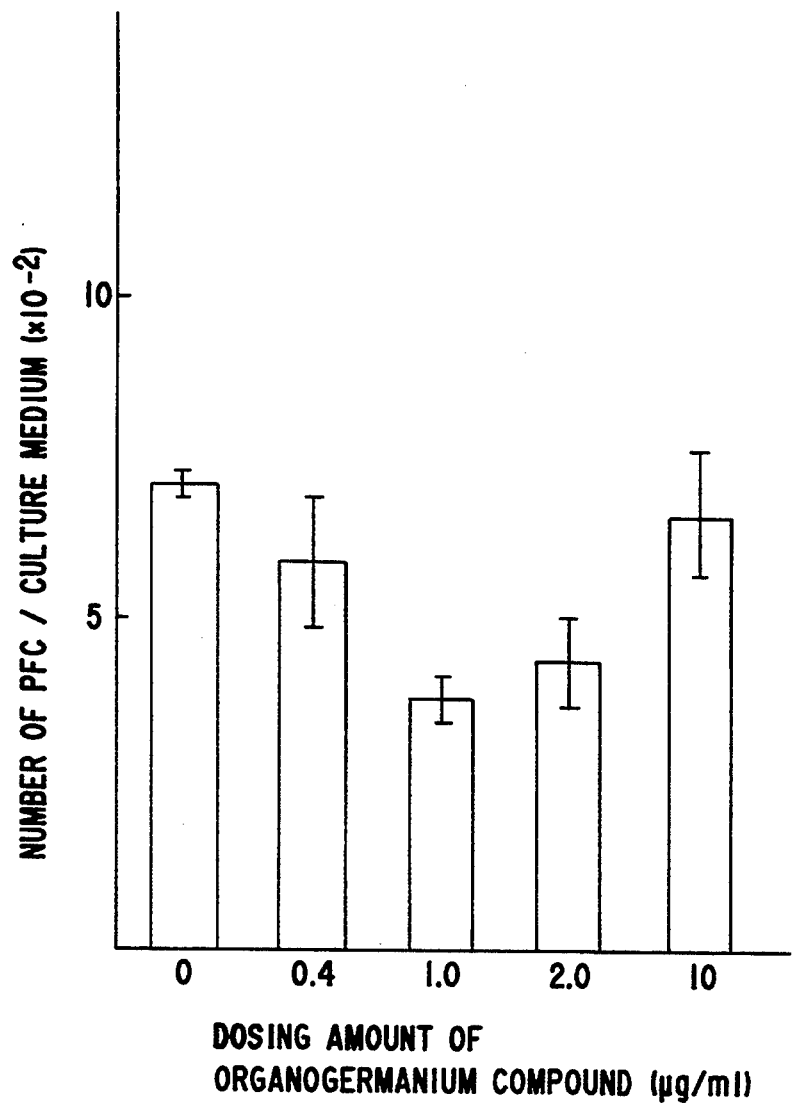
FIG. 10a is a set of graphs showing the influence of this same original compound on antibody production ability in NZB/W $F_1$ mice.
Figure 10B:
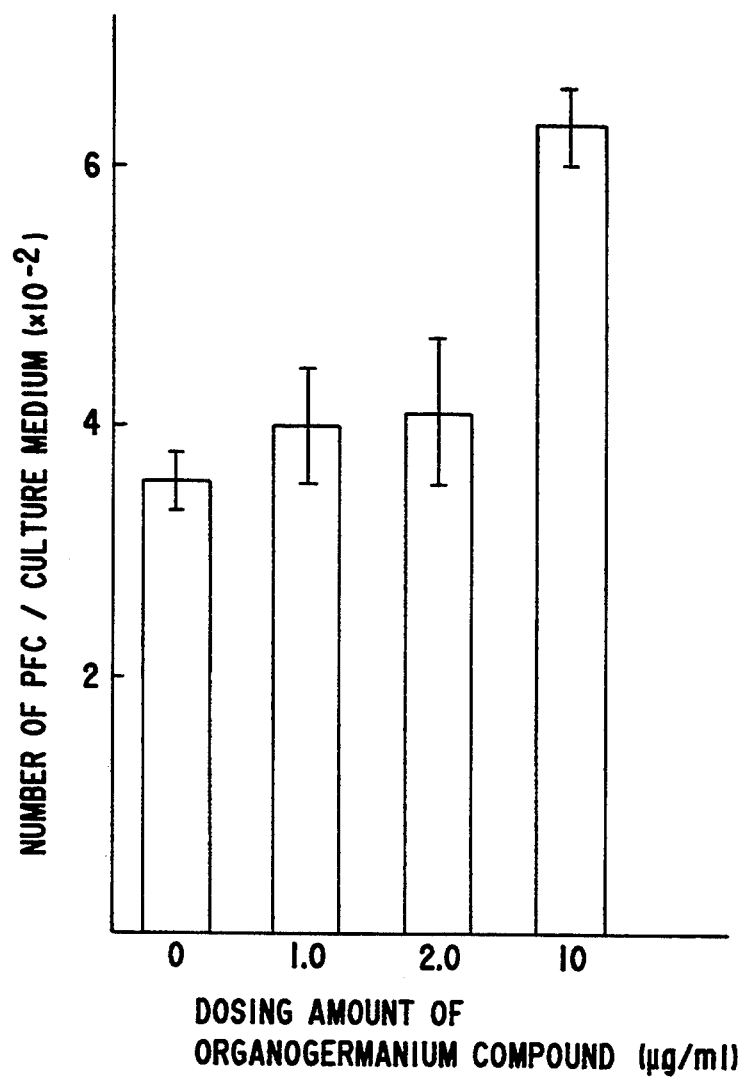
FIG. 10b is a set of graphs showing the influence of this same original compound on antibody production ability in BALBC/c mice.

Results are shown in FIGS. 10a and 10b. From the figures, an inhibition in antibody production ability is recognized on the NZB/W $F^1$ mouse lymphocytes, when the organogermanium compound is added in the amount of 1 to 2 μg/ml (FIG. 10a) but on the BALB/C mouse lymphocytes, no change can be recognized in antibody producing function by adding the organogermanium compound in such amount and on contrary thereto, an accelation of the function can be seen, when the compound is added in the amount of 10 μg/ml (FIG. 10b).

These results also show apparently that a pharmacological action of the organogermanium compound to the immunity system is immunity adjusting one.

Pharmacological Test Example 4

Action of organogermanium compound to positive Arthus reaction in guinea pig a) Object For studying a usability of the organogermanium compound (Compound No. 1 in Table 1) to an allergic parietitis, an action thereof to an active Arthus reaction in guinea pig is checked.

b) operation

To 2% egg albumin solution, a same amount of Freund's complete adjuvant was added to prepare an emulsion. The emulsion was injected in 4 times by one time/week to Hartley male guinea pigs at a heel, under a skin and in the femoralis muscle, for sensitization. After 10 days from the final sensitization, 0.1 ml of 1% egg albumin solution was injected under a skin of the back to measure an area of resulting edema. The organogermanium compound was orally dosed for 30 days from the first sensitization in an amount of 0.1, 1.0 and 10 mg/kg/day.

c) Results

Figure 11:
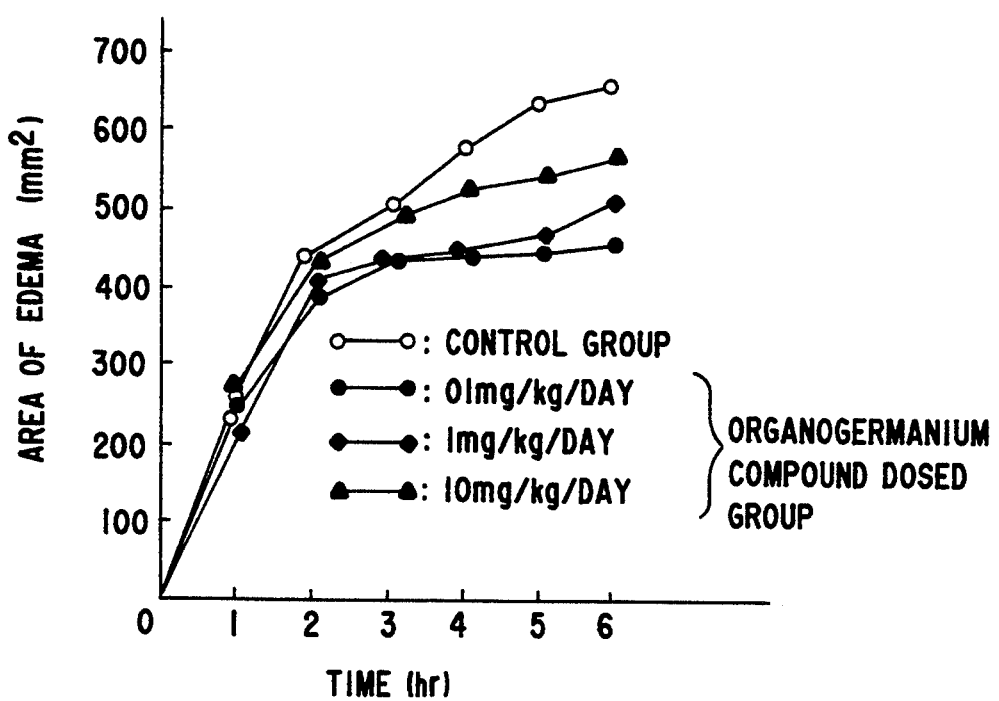
FIG. 11 is a series of plots showing the influence of this same original compound on positive Arthus reaction in guinea pigs.

Each change in the edema area is shown in FIG. 11. From the figure, a recognizable inhibition of the phlegmasia can be found in the groups, to which the organogermanium compound was dosed in a ration of 0.1 and 1 mg/kg/day, respectively.

Pharmacological Test Example 5

Action of organogermanium compound to adjuvant arthritis a) Object

An effect of the organogermanium compound (Compound No. 1 in said Table 1) to a prevention of an adjuvant arthritis is checked.

b) Operation 0.05 ml of an adjuvant (prepared by suspending 0.6 mg of micobacteriumbutircum into 0.05 ml of liquid paraffin) was injected under a skin of hind leg heel in S.D. male rats. After 1, 3, 5, 7, 21, and 28 days from the adjuvant dosage, a volume of the dosed and non-dosed legs was measured to determine a ratio of the edema.

The organogermanium compound was orally dosed for 28 days from the adjuvant dosage, in an amount of 1, 10 and 100 mg/kg/day, respectively.

c) Results and consideration

Figure 12:
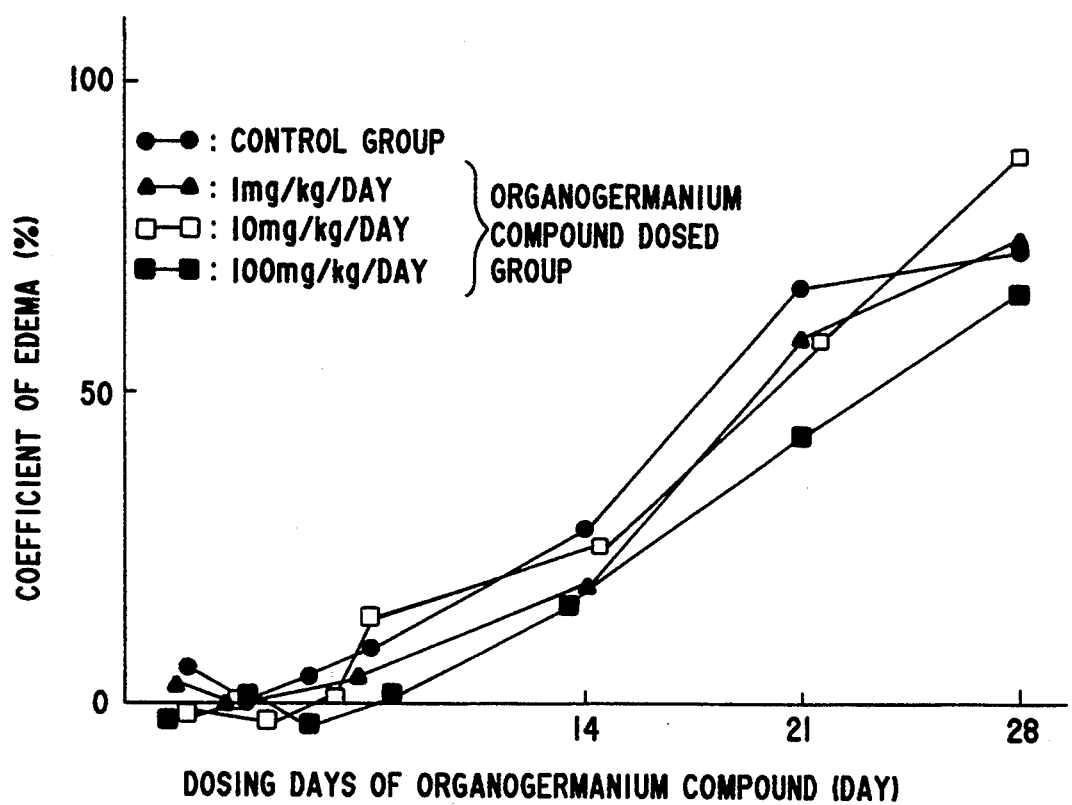
FIG. 12 is a series of plots showing the influence on this same original compound on adjuvant arthritis in rats.

Results are shown in FIG. 12. From the figure, an inhibition effect to a secondary phlegmasia after 14 to 28 days can be recognized in the group, to which the organogermanium compound was dosed in the amount of 100 mg/kg/day.

REFERENCE EXAMPLE 1

Preparation of Stabilized Polymer composition

Into a 0.5% aqueous solution of gelatin was added 3-oxygermylpropionic acid (Compound 1, Table 1) in an amount to produce a 0.5% (w/v) solution. The mixture was stirred until completely dissolved and the solution was freeze dried to obtain a stabilized polymeric composition.

REFERENCE EXAMPLE 2

Preparation of a Stabilized Polymer Composition

Into a 9% aqueous solution of lactose was added 3-oxygermylpropionic acid (Compound 1, Table 1) in an amount sufficient to produce a 1% (w/v) solution and the mixture was stirred until completely dissolved. The solution was freeze dried to obtain the desired stabilized polymeric composition.

REFERENCE EXAMPLE 3

Preparation of Stabilized Polymer Composition

A stabilized polymer composition was obtained in the same manner as in reference Example 2, except that the starting solution was a 0.5% aqueous solution of hydroxypropylcellulose and the solution was spray-dried.

REFERENCE EXAMPLE 4

Preparation of Stabilized Polymer composition

A stabilized polymer composition was obtained in the same manner as in reference example 3, except that the starting solution was a 0.5% aqueous solution of hydroxypropylmethylcellulose.

PHARMACEUTICAL AGENT PREPARATION EXAMPLE 1

Injection

To 0.1% solution of sodium carboxymethylcellulose, the organogermanium compound (Compound No. 1 in Table 1) was added to make a concentration of the organogermanium compound to 1.5% and then mannitol was made into 2%. The resulting solution was sterilized by filtration and filled into each vial by 2 ml, and freeze dried to prepare a powder for preparing an injection.

The powder can be dissolved into isotonic sodium chloride before use.

PHARMACEUTICAL AGENT PREPARATION EXAMPLE 2

Lotion for external application

The organogermanium compound (Compound No. 1 in Table 1) was added into 0.5% solution of polyvinylpyrrolidone and dissolved therein to make a concentration of the organogermanium compound to 0.1%

This solution can directly be applied on skin or mucosa for a therapeutic purpose.

PHARMACEUTICAL AGENT PREPARATION EXAMPLE 3

Cream for external application

The organogermanium compound (Compound No. 1 in Table 1) was added into 4% solution of bovine serum albumin and dissolved therein to make a concentration of the organogermanium compound to 1.0%, and then the solution was freeze dried. This freezed dry powder composition was mixed with excipient in a following prescription to prepare a cream agent (ointment).

| | |
|---|---|
| the powder composition | 0.5 (g) |
| diethyl sebacate | 8.0 |
| spermaceti | 5.0 |
| sodium polyoxyethyleneoleyletherphosphate | 6.0 |
| sodium benzoate | 0.5 |
| petrolatum | a sufficient quantity |
| Total | 100 (g) |

PHARMACEUTICAL AGENT PREPARATION EXAMPLE 4

Suppository

The freezed dry composition in Pharmaceutical Agent Preparation Example 3 was dispersed in melted high fatty acid glycerides in following amount ratio and suppositories were directed from the dispersion, in conventional method.

| | |
|---|---|
| the Powder Composition | 60 (mg) |
| fatty base (cacao butter) | 1640 |
| | 1700 (mg)/piece |

PHARMACEUTICAL AGENT PREPARATION EXAMPLE 5

Tablet

The organogermanium compound (Compound No. 1 in Table 1) was added and dissolved in 1% aqueous solution of pepsin, to make a concentration of the organogermanium compound to 1% and then the solution was freeze dried.

The freezed dry composition was mixed with excipients in a following prescription to prepare tablets in a conventional method.

| | |
|---|---|
| the powder composition | 60 (mg) |
| lactose | 90 |

-continued

| calcium carboxymethylcellulos | 7 |
| light anhydrous silicic aced | 1 |
| magnesium stearate | 7 |
| | 165 (mg)/tablet |

PHARMACEUTICAL AGENT PREPARATION EXAMPLE 6

Capsule

The freezed dry composition in the Pharmaceutical Agent Preparation Example 5 was mixed with other ingredients in a following prescription and this mixture as filled into each hard gelatin capsule, in a conventional method to prepare capsuled agent.

| the powdered composition | 30 (mg) |
| lactose | 107 |
| hydroxypropylmethylcellulose | 2 |
| magnesium stearate | 1 |
| | 140 (mg)/capsule |

PHARMACEUTICAL AGENT PREPARATION EXAMPLE 7

Capsule

Capsules were prepared in a conventional manner using the following ingredients in the listed amounts:

| Stabilized polymer composition (Ref. Ex. 1) | 40 (mg) |
| lactose | 107 |
| hydroxypropylmethylcellulose | 2 |
| magnesium stearate | 1 |
| | 150 mg/capsule |

PHARMACEUTICAL AGENT PREPARATION EXAMPLE 8

Tablet

Tablets were prepared in a conventional manner by compounding the following ingredients in the listed amounts and tableting same:

| Stabilized polymer composition (Ref. Ex. 2) | 100 mg |
| lactose | 50 |
| calcium carboxymethylcellulose | 7 |
| light anhydrous silicic acid | 1 |
| magnesium stearate | 7 |
| | 165 mg/tablet |

PHARMACEUTICAL AGENT PREPARATION EXAMPLE 9

Powder

Powders were prepared by mixing the following ingredients in the amounts indicated:

| stabilized polymer composition (Ref. Ex. 3) | 60 mg |
| lactose | 940 |
| | 1000 mg/pkg. |

PHARMACOLOGICAL AGENT PREPARATION EXAMPLE 10

Granule

Granules were obtained in a conventional wet—granulation method using ethanol and water and the ingredients and amounts listed as follows:

| stabilized polymer composition (Ref. Ex. 4) | 55 mg |
| lactose | 685 |
| corn starch | 250 |
| hydroxypropylcellulose | 10 |
| | 1000 mg/pkg |

IN VIVO UTILIZATION EXAMPLE 1

The external cream agent obtained in Pharmaceutical Agent Preparation Example 3 was given to 20 volunteers who have a red swelling due to a stinging by an insect, food allergy, pain or itching due to piles or the like local disease to use the same, as required. After a specified time period, a questionnaire was distributed and analyzed to obtain results as shown in following Table 3. As seen from the Table, almost all, persons answered to the effect that the cream agent has a beneficial effect.

IN VIVO UTILIZATION EXAMPLE 2 a) Objects

Effects of the organogermanium compound are checked by giving the capsule as obtained in the Pharmaceutical Composition Preparing Example 7 to 6 patients infected by HIV (human Immunodeficiency Virus), who are male hemophiliacs (Age: 6 to 22 years old) recognized as asymptomatic carriers, and among them 5 patients are positive to HIV and 1 patient is negative to HIV.

b) Operations and Items of Inspection

To each patient, the capsule was given in a dose of 80 mg/day for the patient of 10 years old or over and 40 mg 1 day for the patient less than 10 years old, for 9 months. The number of blood lymphocytes, $OKT_4$-value, $OKT_8$-value and $OKT_{4/8}$ ratio, as well as change the virus marker (HIV, HIV antigen and HIV antibody) in blood of the patients were monitored. The separation of the HIV was carried out in accordance with the CDC (Communicable Disease Center) method, and a measurement of the HIV antigen was carried out using the Western blotting method.

c) Results and consideration i) Lymphocytes

No noticeable change has been observed on the number of lymphocytes, as shown below:

Before: $2430 \pm 311/\mu l$, and

After 6 months: $2349 \pm 312/\mu l$.

ii) $OKT_4$-value

Change in the $OKT_4$-value Is as follows.

Before: $463 \pm 64/\mu l$,

After 2 months: $549 \pm 89/\mu l$, and

After 6 months: $629 \pm 97/\mu l$.

Although this shows a certain increasing tendency in the value, it has been found that a value in the normal range at the time of first measurement shall not so change in level through the testing time period. A value at a lower level at the first stage apparently increases, and a value at a higher level at the first stage apparently decreases.

iii) OKT$_8$-value

Change in the OKT$_8$-value is as follows.

Before: $1303 \pm 174/\mu l$, and

After 6 months: $1154 \pm 153/\mu l$.

Although this shows a certain decreasing tendency in the value, it has been found that the value in each group shows the tendencies similar to those in OKT$_4$-value.

iv) OKT$_4$/$_8$ ratio

Change in the ratio is as follows.

Before: $0.36 \pm 0.03$,

After 1 month: $0.42 \pm 0.02$,

After 3 months: $0.51 \pm 0.06$, and

After 6 months: $0.54 \pm 0.05$.

The shows a slow increase in the ratio.

From the above i) to iii), it has been estimated that the organogermanium compound shows an anti-viral action through the immune system and more particularly, acts on T-cells and MO to adjust the immune response.

v) Change in virus marker on HIV positive patients

Through the testing period of time over 9 months, no change has been observed on 2 persons among 5 HIV positive patients, but HIV disappeared on other 3 persons, by the dosage of the compound over 6 months, as shown in the Table given below.

Some increase in appetite and body weight have been recognized on 2 persons, but clinical observation did not show any sideeffect.

| Patient | Item | Week(s) | | | Months | | |
|---|---|---|---|---|---|---|---|
| | | −5 | 0 | 2 | 6 | 7 | 9 |
| A | HIV separation | | + | + | − | − | − |
| | HIV antigen | | − | − | − | − | − |
| | HIV antibody | | + | + | + | + | + |
| B | HIV separation | + | + | + | − | − | − |
| | HIV antigen | + | + | + | + | + | + |
| | HIV antibody | + | + | + | + | + | + |
| C | HIV separation | | + | + | − | − | − |
| | HIV antigen | | + | + | + | + | + |
| | HIV antibody | | + | + | + | + | + |

We claim:

1. A method of stabilizing an organo germanium polymer having the formula:

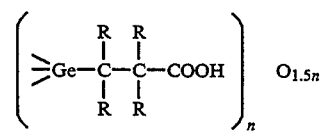

against hydrolysis upon contact with water, which method comprises admixing such compound with a stabilizing amount of about 0.5 to 10% by weight of at least one high molecular weight compound selected from the group consisting of gelatin, lactose, hydroxypropyl cellulose, hydroxypropyl methyl cellulose, serum, serum albumen, polyvinyl pyrrolidone and pepsin.

2. A method of stabilizing an organogermanium polymer as claimed in claim 1 wherein said polymer is present in said admixture in a proportion of about 0.01 to 1 weight percent thereof.

* * * * *